United States Patent [19]

Strom

[11] Patent Number: 4,532,218

[45] Date of Patent: Jul. 30, 1985

[54] IDENTIFICATION OF CARBON-CONTAINING IONS ADSORBED ON ION-EXCHANGE RESINS BY NUCLEAR MAGNETIC RESONANCE SPECTROSCOPY

[75] Inventor: E. Thomas Strom, Dallas, Tex.

[73] Assignee: Mobil Oil Corporation, New York, N.Y.

[21] Appl. No.: 278,548

[22] Filed: Jun. 29, 1981

[51] Int. Cl.³ .............................................. G01N 24/08
[52] U.S. Cl. ..................................... 436/82; 324/300; 436/173
[58] Field of Search ........................ 436/82, 173, 145; 324/300

[56] References Cited

U.S. PATENT DOCUMENTS 3,420,634  1/1969  Godsey ........................... 436/173 X
3,954,410  5/1976  Pohl et al. ........................... 436/173

OTHER PUBLICATIONS

Strom et al., J. Am. Chem. Soc., vol. 103, No. 5, Mar. 1981, 1255–1256.
Boutard et al., Chemical Abstracts, vol. 85, 1976, No. 85:54291u.
Boutard, Chemical Abstracts, vol. 87, 1977, No. 87:60365d.
Moniz et al., Report of NRL Progress pp. 1–14, Aug. 1975, Published by US Dept. of Commerce, National Technical Information Service, 5285 Port Royal Road, Springfield, Va. 22151 USA.
Gromov et al., Chemical Abstracts, vol. 87, 1977, No. 87:91186a.
Franca et al., Chemical Abstracts, vol. 87, 1977, No. 87:91187b.
"Proton–enhanced NMR of Dilute Spins in Solids*", by Pines, M. G. Gibby, & J. S. Waugh, *The Journal of Chemical Physics*, vol. 59, No. 2, pp. 569–590.
"A First Step Toward High Resolution $^{13}$C NMR, Spectroscopy of Intractable Polymers, Epoxies", by H. A. Resing & W. B. Moniz, Notes, vol. 8, 1975, pp. 560–561.

*Primary Examiner*—Arnold Turk
*Attorney, Agent, or Firm*—Alexander J. McKillop; Michael G. Gilman; Charles J. Speciale

[57] ABSTRACT

A process for the detection of carbon-containing ions, particularly uranyl tricarbonate, adsorbed on an ion-exchange resin, comprising introducing a sample of the ion-exchange resin to nuclear magnetic resonance (nmr) spectroscopy.

5 Claims, 6 Drawing Figures

∼ 0.1 M 90% NA₂C¹³O₃
300 pulses 168.86 ppm

∼ 0.1 M 90% Na₂C¹³O₃ + 1 cc Dowex 21K
anion-exchange resin beads
250 pulses 168.35 ppm 168.09 ppm Washed Dowex 21K anion-exchange
resin beads
250 pulses 168.41 ppm

IDENTIFICATION OF CARBON-CONTAINING IONS ADSORBED ON ION-EXCHANGE RESINS BY NUCLEAR MAGNETIC RESONANCE SPECTROSCOPY

FIELD OF THE INVENTION

This invention relates to the spectral analysis of carbon-containing ions adsorbed on ion-exchange resins by carbon-13 nuclear magnetic resonance spectroscopy.

BACKGROUND OF THE INVENTION

Ion-exchange resins are widely used for the isolation and purification of commercially significant ionic species. Due to the difficulties of working with heterogeneous systems, methods of studying ions directly adsorbed on ion-exchange resin beads are limited. Carbon-13 nuclear magnetic resonance has the powerful capability of being able to identify molecular structures in amazing detail. A carbon-13 identification of a carbon-containing ion directly adsorbed on ion-exchange resins may in many cases be definitive.

Ion-exchange resins are used to adsorb uranium carbonate complexes in uranium extraction process streams used in the recovery of uranium. The recovery of uranium from uranium ores conventionally involves leaching the ores with an acid or basic solution. The formation of the soluble and extremely stable uranyl tricabonate anion, $UO_2(CO_3)_3{}^{4-}$, however, makes the use of alkali and ammonium carbonate salts particularly advantageous in the leaching process. In the standard procedure, the solution and/or slurry resulting from the leaching process is, in turn, contacted with a strong base anionic-exchange resin such as Dowex 21K (tradename for strong base anionic resin manufactured by Dow Chemical) on which the uranyl tricarbonate anion is directly adsorbed to thereby isolate the uranium. It would therefore be very much desired to be able to monitor the presence and concentration of the uranium complexes loaded on the anion-exchange resins for determining the nature of the process stream.

SUMMARY OF THE INVENTION

The present invention relates to a process for the detection of carbon-containing ions having a nuclear magnetic resonance active nucleus adsorbed on ion-exchange resins comprising subjecting the ion-exchange resin suspected of containing the carbon-containing ions to analysis by nuclear magnetic resonance spectroscopy.

In one embodiment of the present invention, there is provided a process for detecting and monitoring the occurrence and concentration of uranyl tricarbonate, carbonate, and bicarbonate anion carbons adsorbed on a Dowex 21K anion-exchange resin.

DETAILED DESCRIPTION OF THE INVENTION

Figure 1:
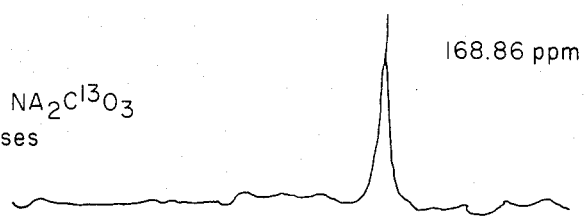
FIG. 1 represents the carbon-13 nmr spectra of a carbonate ion, $CO_3{}^{--}$, prior to adsorption on a specific anionic resin at a pH of about 10.8.

Nuclear magnetic resonance techniques (nmr) provide a powerful means of not only distinguishing between atoms of differing chemical environments, but also determining their concentrations. Conventional high resolution nmr techniques require gaseous or liquid samples since the line broadening effects of magnetic dipole-dipole interactions and chemical anisotropy must be averaged out by molecular tumbling. When a carbon-containing anion is adsorbed on an anion-exchange resin, it is not self-evident that sufficient molecular motional freedom remains to allow the observation of a high resolution nmr spectrum.

In accordance with the present invention, it has been surprisingly discovered that carbon-containing ions, such as uranyl tricarbonate, carbonate, and bicarbonate adsorbed on an ion-exchange resin, can be unambiguously identified in water solutions utilizing C-13 nuclear magnetic resonance spectroscopic analysis. In the case of uranyl tricarbonate adsorbed on Dowex 21K, an anion-exchange resin, the resonance peak of the uranyl tricarbonate appears at $168.9 \pm 0.2$ ppm to the left of the standard reference, tetramethyl silane (TMS), at a pH of about 9.3.

In order to enable those skilled in the art to better understand how the present invention is practical, the following example is offered by way of illustration and not by way of limitation.

EXAMPLE 1

Experiments were conducted in which the carbon-13 nmr spectra were obtained from a uranyl tricarbonate anion, $UO_2(CO_3)_3{}^{4-}$, adsorbed on a specific anion-exchange resin, Dowex 21K. A solution was made up containing ~0.03M 90% carbon-13 labeled uranyl tricarbonate in the presence of an excess of 90% carbon-13 labeled bicarbonate in 75% $H_2O$—25% $D_2O$. The solution was yellow because of the presence of the uranyl tricarbonate ion. A 15 MHz carbon-13 nmr spectrum taken on a JEOL FX60 nmr spectrometer showed two peaks present from the $UO_2(CO_3)_3{}^{4-}$ and $HCO_3{}^-$ species. Using a sealed internal reference of 90% $C^{13}H_3OH$, whose chemical shift was taken as 49.3 ppm to the left of the standard tetramethyl silane reference, the uranyl tricarbonate peak occurred at $168.9 \pm 0.2$ ppm and the bicarbonate peak at $163.1 \pm 0.2$ ppm at pH=9.3. The relative amounts of both species are measured by electronic integration.

To 5 ml of the above solution in a 10 mm nmr tube was added 1 cc of Dowex 21K anion-exchange resin beads in the chloride form. After one hour, the yellow color of the solution was much lighter. Both species were still seen in the carbon-13 nmr spectra, the uranyl tricarbonate at $168.9 \pm 0.2$ ppm and the bicarbonate at $162.8 \pm 0.2$ ppm. However, the uranyl tricarbonate peak had become more abundant than the bicarbonate peak, as shown by an electronic integration.

After two hours, the solution was colorless. A carbon-13 nmr spectra showed that both species were still present, the uranyl tricarbonate at 168.9±0.2 ppm and the bicarbonate at 162.8±0.2 ppm, but the electronic integral showed that uranyl tricarbonate was still more abundant than the bicarbonate.

When the ion-exchange beads were filtered from the solution, rinsed off with distilled water, put back in an nmr tube with a little distilled water, and the carbon-13 nmr taken again, a spectrum was obtained at 168.9±0.2 ppm from the uranyl tricarbonate complex.

These experiments clearly validate the concept given above. All of the beads were in the nmr active part of the cavity, while part of the solution extends above the nmr active part of the cavity. Since uranyl tricarbonate has four negative charges compared to bicarbonate's one, it was preferentially loaded on the anion-exchange resin. Therefore, uranyl tricarbonate was preferentially drawn in to the nmr active part of the cavity. This was also demonstrated by the disappearance of the yellow color. This accounts for the integral showing of a much larger ratio of uranyl tricarbonate to bicarbonate.

EXAMPLE 2

Experiments were conducted in which the carbon-13 nmr spectra were obtained on a carbonate ion, $CO_3^{--}$, adsorbed on a specific anion-exchange resin, Dowex 21K. A solution was made up containing ~0.1M 90% carbon-13 labeled sodium carbonate, $Na_2CO_3$, in 75% $H_2O$—25% $D_2O$. The pH of the solution was about 10.8. A carbon-13 nmr spectrum showed a single peak at 168.86±0.2 ppm as shown in FIG. 1.

Figure 2:
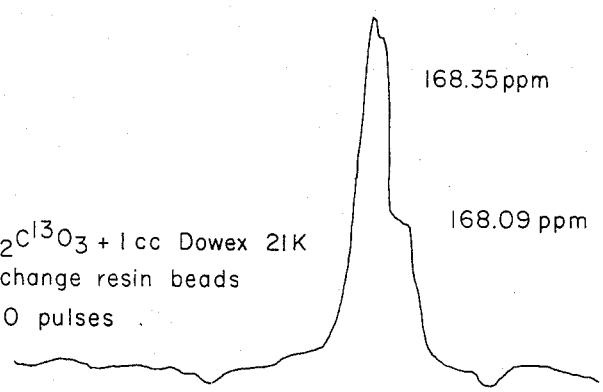
FIG. 2 represents the carbon-13 nmr spectra of carbonate ions in contact with a specific anionic resin wherein a portion of the ions are adsorbed on the resin.
Figure 3:
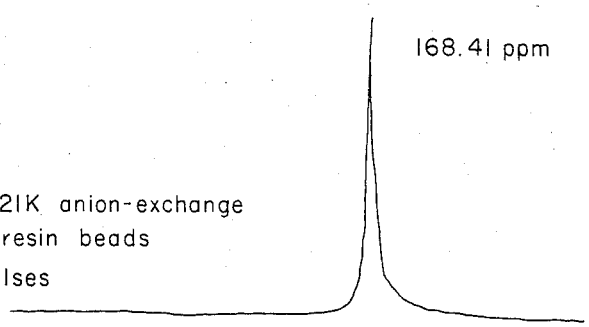
FIG. 3 represents the carbon-13 nmr spectra of carbonate ions adsorbed on a specific anionic resin.

To 5 ml. of the above solution in a 10 mm nmr tube was added 1 cc of Dowex 21K anion-exchange resin beads in the chloride form. After 15 minutes, another carbon-13 nmr spectrum was taken. This time the spectrum showed two overlapping peaks, a taller peak at 168.35±0.2 ppm and a smaller peak at 168.1±0.2 ppm as shown in FIG. 2. The beads were filtered from the solution, rinsed off with distilled water, put back in an nmr tube with a little distilled water, and the carbon-13 nmr spectrum taken again. A spectrum was obtained with a single peak at 168.41±0.2 ppm as shown in FIG. 3. This peak, within experimental error, is identical to the taller peak at 168.35±0.2 ppm shown in FIG. 2 and clearly comes from carbonate adsorbed on anion-exchange resin beads.

The peak at 168.1 ppm comes from $CO_3^{--}$ in bulk water. Its position is shifted from the 168.9 ppm found prior to bead addition because of a pH effect. The addition of 1 cc of Dowex 21K anion-exchange resin beads to 5 ml of 0.1M $Na_2CO_3$ lowers the pH 0.4–0.5 units. This pH lowering decreases the amount of $CO_3^{--}$ present by a small amount through the formation of a small amount of $HCO_3^-$. Since $HCO_3^-$ has a different chemical shift (~162 ppm) than $CO_3^{--}$ (~169 ppm), the increased amount of $HCO_3^-$ lowers the chemical shift.

EXAMPLE 3

Figure 4:
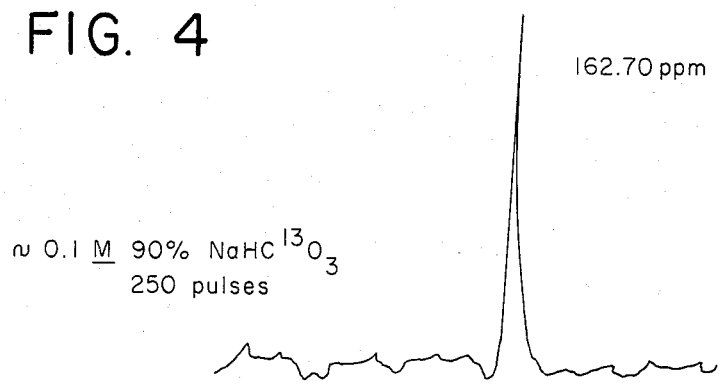
FIG. 4 represents the carbon-13 nmr spectra of a bicarbonate ion, $HCO_3{}^-$, prior to adsorption on a specific anionic resin at a pH of about 9.0.

Experiments were conducted in which the carbon-13 nmr spectra were obtained on a bicarbonate ion, $HCO_3^-$, adsorbed on a specific anion-exchange resin, Dowex 21K. A solution was made up containing 0.1M 90% carbon-13 labeled sodium bicarbonate. The pH of the solution was about 9.0. A carbon 13 nmr spectrum showed a single peak at 162.70±0.2 ppm as shown in FIG. 4.

Figure 5:
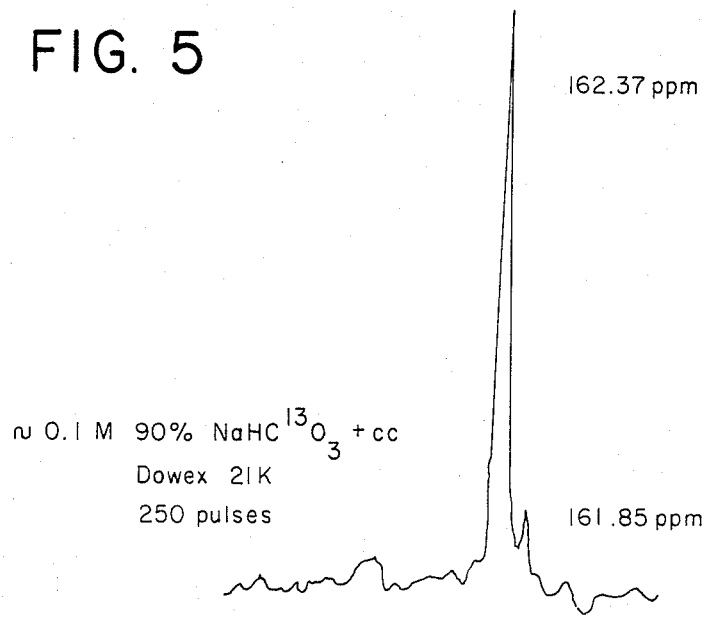
FIG. 5 represents the carbon-13 nmr spectra of bicarbonate ions in contact with a specific anionic resin wherein a portion of the ions are adsorbed on the resin.
Figure 6:
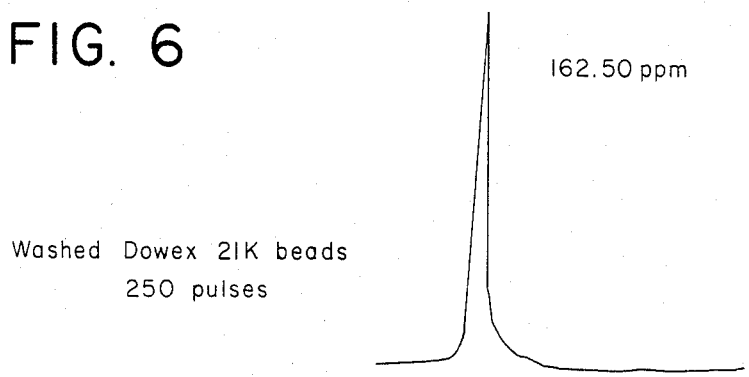
FIG. 6 represents the carbon-13 nmr spectra of bicarbonate ions adsorbed on a specific anionic resin.

To 5 ml of the above solution in a 10 mm nmr tube was added 1 cc of Dowex 21K anion-exchange resin beads in the chloride form. After 15 minutes, another carbon-13 nmr spectrum was taken. This time the spectrum showed two peaks, a much taller peak at 162.37±0.2 ppm and a very small peak at 161.85±0.2 ppm as shown in FIG. 5. The beads were filtered from solution, rinsed off with distilled water, put back in an nmr tube with a little distilled water, and the carbon-13 nmr spectrum taken again. A spectrum was obtained with a single peak at 162.50±0.2 ppm as shown in FIG. 6. This peak, within experimental error, is identical to the taller peak at 162.37±0.2 ppm of FIG. 5 and clearly comes from bicarbonate adsorbed on anion-exchange resin beads. The shift of $HCO_3^-$ in bulk water from 162.70±0.2 ppm stems from a reduction in pH from bead addition as described in Example 2.

The concentration of ion actually loaded on the resin bead can be ascertained by spiking the bead-water mixture with a known concentration of a known carbon-containing compound having a nmr active nucleus that does not adsorb on an ion-exchange resin.

One possible standard for use with the bead-water mixture would be the organic molecule, para-dioxane. This molecule is miscible with water in all proportions. It has four carbon atoms which are magnetically equivalent with a chemical shift that is concentration-dependent but is around 67.4 ppm, well outside the range of interference with uranyl tricarbonate, carbonate, or bicarbonate.

The process of the present invention can be adapted to simple, inexpensive, nmr instruments, particularly dedicated carbon-13 Fourier transform nmr instruments, and to carbon-13 in natural abundance by using long acquisition times.

Obviously, other modifications and variations of the present invention are possible in the light of the above teachings. It is, therefore, to be understood that changes may be made in the particular embodiments of this invention which are within the full intended scope of the invention as defined by the appended claims.

For example, by obvious extensions of the methods described herein, other carbon-containing ions that load on ion-exchange resins may be monitored.

Furthermore, depending on their relaxation times, chemical shifts, and chemical shift anisotropies, other magnetically-active nuclei loaded on anion-exchange resins may also be monitored by Fourier-transform multi-nuclear nmr. Some specific examples offered here by way of illustration and not limitation are fluorine-19 in fluoride or some other fluorine-containing anion, phosphorus-31 in phosphate or some other phosphorus-containing anion, and non-exchangeable protons in any hydrogen-containing anion. These techniques should also be applicable to nmr-active nuclei in cations loaded on cation-exchange resins.

I claim:

1. A process for the identification of a uranyl carbonate adsorbed on an anion-exchange resin and having a nuclear magnetic resonance active nucleus, said process comprising placing an anion-exchange resin suspected of having adsorbed a uranyl carbonate in a nuclear magnetic resonance tube with distilled water and then subjecting the anion-exchange resin in the nuclear magnetic resonance tube to C-13 Fourier transform nuclear magnetic resonance spectroscopic analysis to indicate the presence of a uranyl carbonate adsorbed on said resin.

2. A process according to claim 1 wherein said uranyl carbonate is uranyl tricarbonate.

3. A process according to claim 1 wherein said anion-exchange resin is Dowex 21K.

4. A process according to claim 1 including the further step of determining the concentration of said carbon-containing ion.

5. A process according to claim 4 wherein the ion-exchange resin is spiked with a known carbon-containing compound having a nmr active nucleus that does not adsorb on the resin.

* * * * *